United States Patent [19]

Montanari

[11] 4,376,788

[45] Mar. 15, 1983

[54] BASIC ETHERS OF 4-HYDROXY-BENZOPHENONES ACTING AS BETA-BLOCKING AGENTS

[75] Inventor: Roberto Montanari, Milan, Italy

[73] Assignee: Stabilimento Bioterapico Farmacologico La Farmochimica Italiana, S.p.A., Milan, Italy

[21] Appl. No.: 233,948

[22] Filed: Feb. 12, 1981

[30] Foreign Application Priority Data

Feb. 13, 1980 [IT] Italy .................................. 19887 A/80

[51] Int. Cl.³ ...................... C07C 97/10; A61K 31/135
[52] U.S. Cl. ...................................... 424/330; 564/324
[58] Field of Search ...................... 564/328, 329, 348; 260/348.15; 424/330

[56] References Cited

U.S. PATENT DOCUMENTS

| | | | |
|---|---|---|---|
| 3,102,839 | 9/1963 | Neracher et al. | 564/348 |
| 3,553,332 | 1/1971 | Grunberg | 564/328 |
| 3,562,297 | 2/1971 | Howe et al. | 564/348 |
| 3,674,840 | 7/1972 | Elaf et al. | 424/330 |
| 3,930,016 | 12/1975 | Berntsson et al. | 564/348 |
| 4,201,790 | 5/1980 | Basil et al. | 424/330 |
| 4,220,602 | 9/1980 | Kalopissis et al. | 564/348 |
| 4,252,984 | 2/1981 | Manowy et al. | 424/330 |

*Primary Examiner*—Natalie Trousof
*Assistant Examiner*—James H. Reamer
*Attorney, Agent, or Firm*—Anthony Pellicano

[57] ABSTRACT

Basic ethers of 4-hydroxy-benzophenones acting as beta-blocking agents, starting from 4-hydroxy-benzophenones and, by reacting them with epichlorohydrin, transforming them into the corresponding 4-O(2', 3'-epoxy-propoxy) derivatives, then reacting with isopropylamine, obtaining the substances according to the invention which can be defined as 4 (gammaisopropylamino-betahydroxypropoxy) benzophenones, wherein the 3 and 4' positions can be represented by: H, Cl and acetyl.

2 Claims, No Drawings

BASIC ETHERS OF 4-HYDROXY-BENZOPHENONES ACTING AS BETA-BLOCKING AGENTS

The present invention relates to new substances having beta-blocking activity, and particularly basic ethers of 4-hydroxy-benzophenones. There are known from quite a time beta-blocking agents having as general formula:

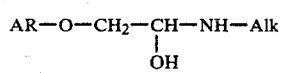

wherein aryl is almost always phenyl, sometimes naphthyl and recently heterocyclic residues.

Alkyl is C1-C4, particularly isopropyl.

The present invention surprisingly proved that, if aryl was equal to benzophenone, and in particular benzophenone 4'-halogen substituted and/or 2-acetyl substituted, some characteristics of the substances were improved with respect to what already known, especially as to the sorption, distribution and elimination rhythms, with the considerable advantages deriving thereof.

Even the salts of the resulting substances obviously fall within the ambit of the present invention, and particularly hydrochlorides, bromhydrates, sulfates, tartrates, lactates and benzoates.

It is an integral part of the present invention a process starting from 4-hydroxy-benzophenones (I) which, through a reaction with epichlorohydrin, are transformed into the corresponding 4-O(2', 3' epoxypropoxy) derivatives (II), and then are reacted with isopropylamine to obtain the substances according to the invention which are 4-(gamma-isopropylamino-betahydroxypropoxy) benzophenones (III).

In these molecules the 3-position (ortho with respect to the basic alkyl chain) and the 4' position can be represented by H, Cl and acetyl.

The process according to the invention can be represented by the following synthesis:

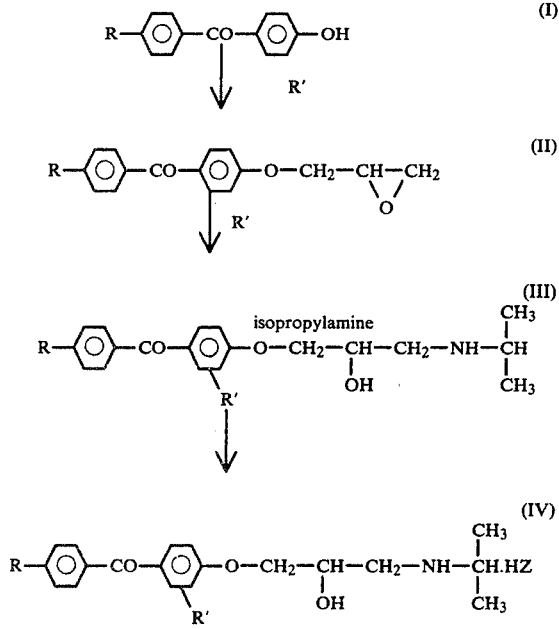

R = H; Cl
R' = H; —COCH$_3$
Z = Cl—; C$_6$H$_5$—COO$^-$

It is to be noted that when passing from II to III it is possible to alternatively sever the bond of the epoxidic function and use the halogen gamma betahydroxypropoxy derivative to obtain, always through a reaction with isopropylamine, the product III.

The present invention could be better understood through the following examples, showing the carrying-out of the process according to the invention.

The pharmacological and clinical effects of known Beta-blocking agents are thoroughly illustrated in these texts:

(1) Clinical pharmacology basic principles in therapeutics, 11 ed. by Kenneth L. Melmon, Havard, F. Morrelli-Publishing Co. Inc.—edited MacMillan, New York 1978, Pagg. 193-196.

(2) The Pharmacological Basis of Therapeutics, 5th ed. edited by Louis S. Goodman and Alfred Gilman, 1975, pagg. 546-552, Publishing Co. Inc.—edited MacMillan.

The products according to invention have been experimented by test called "Blood Pressure and Cardiac Rate Recording in Rabbit After Isoproterenol Injection Intravenous".

By this test the products according to the invention, were found to have same activity as known beta-blocking agents with lower average dosages of 10-20%.

EXAMPLE 1

Preparation of 4-(2',3'-epoxy-propoxy) benzophenones 1 mole of a suitable 4-hydroxybenzophenone is diluted by heating in anhydrous ethanol: while keeping under stirring, a mole of methoxide Na is added. After stirring for 20', the solution is dry concentrated under vacuum. The residue is mixed with 2.5 l of dimethylformamide and 1.5 mole of epichlorohydrin is added thereto; the whole is kept under stirring and heated for 4 hours at 100° C.

Decolorizing carbon is added and, after filtration, the whole is dry concentrated in vacuum. The resulting residue is recrystallized from hexane or aqueous ethanol. The yields range from 75 to 80% of the expected yield.

Starting, e.g., from 4-p.-chlorobenzoyl-phenol and acting as described above, there is obtained 4-chloro-4'-(2,3-epoxy-propoxy)-benzophenone in the form of white crystalline powder ( M.P. 110°-12°), soluble in ethanol, acetone and dioxane, insoluble in water, hexane and petroleum ether.

EXAMPLE 2

Preparation of 4-(2'-oxy-3'-isopropylamino-propoxy) benzophenones 1 mole of a suitable 4-(2,3-epoxy-propoxy) benzophenone (II) is diluted in the minimum alcohol volume, and 3 moles of monoisopropylamine are added. The solution is heated for 8 hours at 35°-40° C., then is left alone overnight at ambient temperature.

After treatment with decolorizing carbon, the bulk mass is dry concentrated in a rotating vacuum evaporator.